United States Patent
Bishop et al.

(10) Patent No.: US 8,361,046 B2
(45) Date of Patent: Jan. 29, 2013

(54) ABSORBENT GARMENTS WITH IMPROVED FIT IN THE FRONT LEG AREA

(75) Inventors: David F. Bishop, Appleton, WI (US);
Russell J. Brumm, Menasha, WI (US);
Patsy A. Krautkramer, Omro, WI (US);
Catherine Marguerite Hancock-Cooke, Neenah, WI (US);
Russell E. Thorson, Appleton, WI (US);
John T. Hahn, Merrill, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 714 days.

(21) Appl. No.: 12/262,348

(22) Filed: Oct. 31, 2008

(65) Prior Publication Data
US 2010/0114048 A1 May 6, 2010

(51) Int. Cl.
*A61F 13/15* (2006.01)
*A61F 13/20* (2006.01)
(52) U.S. Cl. ................ 604/385.22; 604/385.01
(58) Field of Classification Search .......... 604/367, 604/379–380, 383, 384, 385.01, 385.22, 604/385.24–385.25, 385.27, 385.29–385.3
See application file for complete search history.

(56) References Cited

U.S. PATENT DOCUMENTS

| | | | |
|---|---|---|---|
| 4,100,324 A | 7/1978 | Anderson et al. |
| 4,663,220 A | 5/1987 | Wisneski et al. |
| 4,704,116 A | 11/1987 | Enloe |
| 4,940,464 A | 7/1990 | Van Gompel et al. |
| 5,046,272 A | 9/1991 | Vogt et al. |
| 5,104,116 A | 4/1992 | Pohjola |
| 5,114,781 A | 5/1992 | Morman |
| 5,116,662 A | 5/1992 | Morman |
| 5,224,405 A | 7/1993 | Pohjola |
| 5,226,992 A | 7/1993 | Morman |
| 5,284,703 A | 2/1994 | Everhart et al. |
| 5,350,624 A | 9/1994 | Georger et al. |
| 5,486,166 A | 1/1996 | Bishop et al. |
| 5,490,846 A | 2/1996 | Ellis et al. |
| 5,645,542 A | 7/1997 | Anjur et al. |
| 5,766,389 A | 6/1998 | Brandon et al. |
| 5,820,973 A | 10/1998 | Dodge, II et al. |

(Continued)

FOREIGN PATENT DOCUMENTS

| EP | 0217032 A2 | 4/1987 |
|---|---|---|
| WO | WO 0037009 A2 | 6/2000 |

(Continued)

OTHER PUBLICATIONS

Search Report and Written Opinion for PCT/IB2009/053871 dated Apr. 27, 2010, 11 pages.

*Primary Examiner* — Michele M Kidwell
(74) *Attorney, Agent, or Firm* — Dority & Manning, P.A.

(57) ABSTRACT

Absorbent articles with carefully controlled stretch properties are provided. Of particular advantage, the carefully controlled stretch properties can prevent too much tension in the front leg area of the garment. The outer cover is constructed such that the front leg zone has a tension of less than about 1200 grams-force at about 160% to about 175% stretch in the lateral direction, and each of the front waist zone, the front crotch zone, the back crotch zone, the back leg zone, and the back waist zone of the outer cover has a tension of greater than about 1500 grams-force at about 160% to about 175% stretch in the lateral direction. Methods of making such an absorbent article are also provided.

15 Claims, 11 Drawing Sheets

U.S. PATENT DOCUMENTS

| | | |
|---|---|---|
| 5,964,743 A | 10/1999 | Abuto et al. |
| 6,193,701 B1 * | 2/2001 | Van Gompel et al. ... 604/385.01 |
| 6,231,557 B1 | 5/2001 | Krautkramer et al. |
| 6,362,389 B1 | 3/2002 | McDowall et al. |
| 6,367,089 B2 | 4/2002 | Van Gompel et al. |
| 6,552,245 B1 | 4/2003 | Roessler et al. |
| 6,635,041 B1 | 10/2003 | Popp et al. |
| 6,645,190 B1 | 11/2003 | Olson et al. |
| 6,702,800 B1 | 3/2004 | Vukos et al. |
| 6,969,378 B1 | 11/2005 | Vukos et al. |
| 7,699,827 B2 | 4/2010 | Sandin et al. |
| 2001/0007935 A1 | 7/2001 | Gompel et al. |
| 2002/0019616 A1 * | 2/2002 | Thomas ................. 604/373 |
| 2002/0165516 A1 * | 11/2002 | Datta et al. ............ 604/385.16 |
| 2004/0127881 A1 * | 7/2004 | Stevens et al. ......... 604/385.22 |
| 2007/0123834 A1 | 5/2007 | McDowall et al. |
| 2008/0161767 A1 | 7/2008 | Sandin et al. |

FOREIGN PATENT DOCUMENTS

| | | |
|---|---|---|
| WO | WO 0188245 A2 | 11/2001 |
| WO | WO 03051254 A2 | 6/2003 |

* cited by examiner

ABSORBENT GARMENTS WITH IMPROVED FIT IN THE FRONT LEG AREA

BACKGROUND OF THE INVENTION

Absorbent articles such as diapers, training pants, incontinence garments, swim undergarments, and the like conventionally include a liquid permeable body-facing liner, a liquid impermeable outer cover, and an absorbent core. The absorbent core is typically located in between the outer cover and the liner for taking in and retaining liquids (e.g., urine) exuded by the wearer.

In some of these absorbent articles, the articles contain various elastic materials to permit some expansion of the article when necessary to provide a better fit on the wearer. The article is subjected to forces such as those generated by loading of the absorbent article and movement of the wearer during use of the article. The elastic members are also designed to contract when being worn in order to provide the article with form-fitting properties at least in some areas.

When a single piece outer cover is utilized to construct the garment, the front leg area is often subjected to forces that result in this area becoming overly tensioned (e.g., too tight and over stretched), which can result in a poor fit in this area. Adding more material to the outer cover in the front leg area, in an attempt to relieve this tension, results in a baggy fit in the pant which does not look discrete or garment like. Similarly, increasing the size of the leg opening results in less coverage and/or does not relieve the tension and may increase the propensity of the article to leak fluids through the leg opening.

In this regard, improvements are needed in constructing absorbent articles that have form-fitting properties. In particular, a need exists for an absorbent article that has reduced tension in the front leg area, particularly in the front leg area of an absorbent article.

SUMMARY OF THE INVENTION

In general, the present invention relates to disposable absorbent articles having carefully controlled stretch properties. For instance, the absorbent articles may have form-fitting properties resulting in an improved fit and appearance. The carefully controlled stretch properties of the articles can prevent against over tightness in the front leg area after the article has been donned.

An exemplary absorbent article of the present invention can have an outer cover comprising an elastic material, a bodyside liner, and an absorbent structure positioned in between the outer cover and the liner. For explanation purposes, the outer cover defines six equal distant zones in the longitudinal direction: a front waist zone, a front leg zone, a front crotch zone, a back crotch zone, a back leg zone, and a back waist zone. The outer cover is constructed such that the front leg zone has a tension of less than about 1200 grams-force at about 160% to about 175% stretch in the lateral direction, and each of the front waist zone, the front crotch zone, the back crotch zone, the back leg zone, and the back waist zone of the outer cover has a tension of greater than about 1500 grams-force at about 160% to about 175% stretch in the lateral direction.

The present invention is also directed toward a method of making an absorbent article by combining such an outer cover with the absorbent structure and the bodyside liner.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

Figure 1:
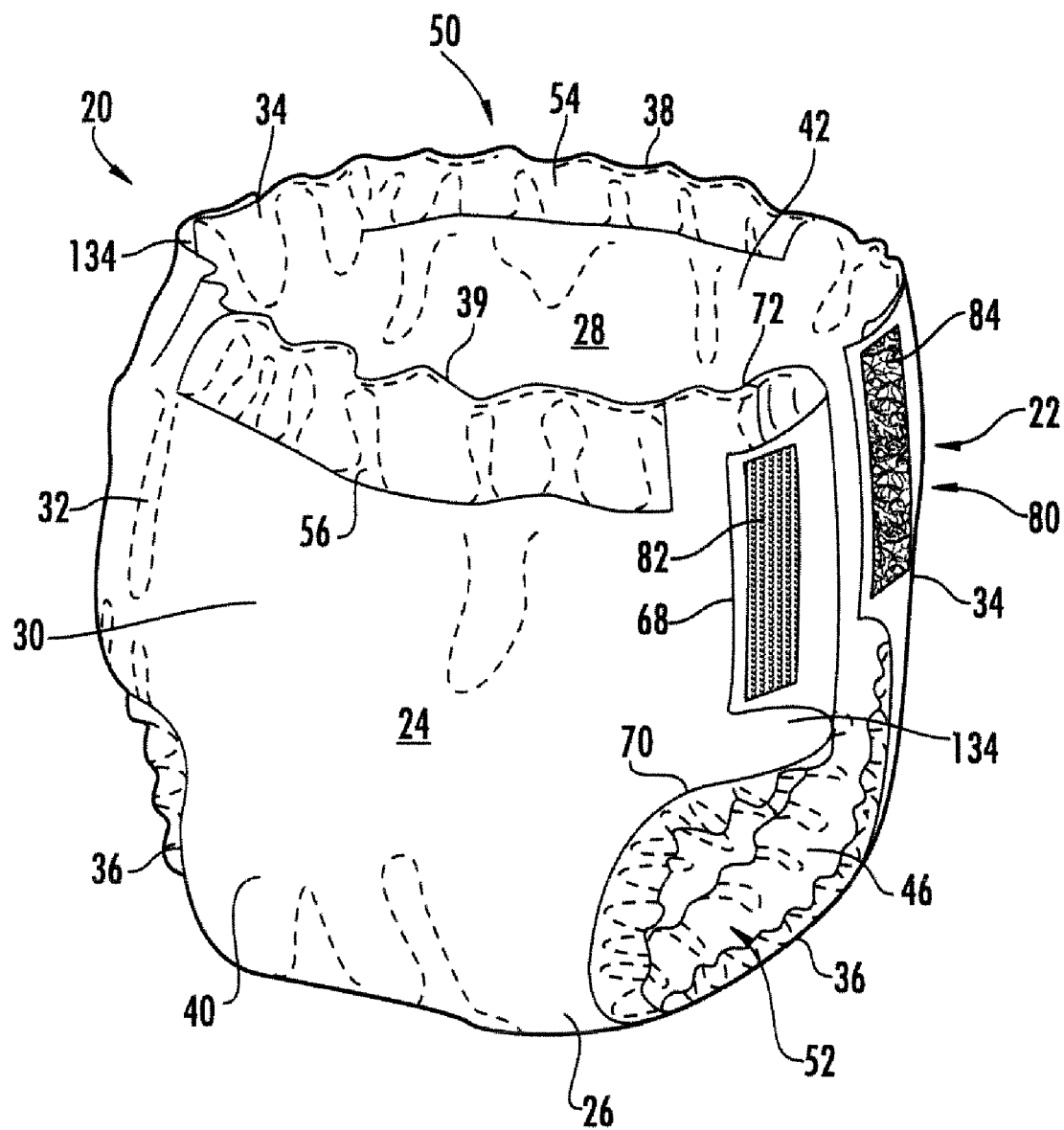
FIG. 1 is a perspective view of one embodiment of an absorbent article made in accordance with the present invention.

Repeated use of reference characters in the present specification and drawings is intended to represent the same or analogous features or elements of the present invention.

DETAILED DESCRIPTION

It is to be understood by one of ordinary skill in the art that the present discussion is a description of exemplary embodiments only, and is not intended as limiting the broader aspects of the present invention.

In general, the present invention is directed to absorbent articles designed to provide improved fit upon donning, especially in the front leg area. The absorbent article may be, for instance, a diaper, a toilet training pant, an adult incontinence garment, a swim undergarment, or the like. In particular, those absorbent articles constructed with a single piece outer cover can have improved fit in the front leg area of the absorbent article. As used herein, the term "single piece outer cover" refers to an outer cover constructed from a sheet or laminate of multiple sheets that extends for the entire outer cover in both the longitudinal and lateral directions of the absorbent article.

Through the above carefully controlled stretch properties, the present inventors have found that absorbent articles exhibit improved fit and appearance. In particular, the stretch properties provide form-fitting properties while also inhibiting excess tension in the front leg area of the article. Thus, the construction of the article allows for a customized fit to a user especially in the lateral direction of the front leg area. Specifically, the stretch properties of the article may accommodate broader or various user shapes. The construction has also been found to facilitate donning of the product.

In general, the absorbent articles are made with stretchable and/or elastic materials. As used herein, the term "stretchable" refers to a material that may be extensible and/or elastic (or elastomeric). That is, the material may be extended, deformed or the like, without breaking, and may or may not significantly retract after removal of an extending force. The terms "elastic" and "elastomeric" are used interchangeably herein and refer to a property of a material where upon removal of an elongating force, the material was capable of recovering to substantially its unstretched size and shape or the material exhibits a significant retractive force. In particular, elastic materials utilized in connection with the present invention may be elongated/extended or stretched in at least one direction without breaking by at least 15%, such as by at least 25% (to at least 125% of its initial unstretched length) in at least one direction, suitably by at least 50% (to at least 150% of its initial unstretched length) and which will recover, upon release of the applied stretching or biasing force, at least 10% of their elongation. It is generally advantageous that the elastomeric material or composite be capable of being elongated by at least 100%, more desirably at least 200%, of its relaxed length and recover at least 30% and more desirably 50% of its elongation upon release of a stretching, biasing force, within about one minute. The term "extensible" refers to a property of a material where upon removal of an elongating force, the material experiences a substantially permanent deformation or the material does not exhibit a significant retractive force.

Referring to FIG. 1, for exemplary purposes, an absorbent article in the form of a training pant 20 that may be made in accordance with the present invention is shown. The training pant 20 may or may not be disposable, which refers to articles that are intended to be discarded after a limited period of use instead of being laundered or otherwise conditioned for reuse. It is understood that the present invention is suitable for use with various other absorbent articles intended for personal wear, including but not limited to diapers, feminine hygiene products, incontinence products, medical garments, surgical pads and bandages, other personal care or health care garments, and the like without departing from the scope of the present invention.

By way of illustration only, various materials and methods for constructing training pants of the various aspects of the present invention are disclosed in PCT Patent Application WO 00/37009 published Jun. 29, 2000 by A. Fletcher et al; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al. which are incorporated herein by reference to the extent they are consistent (i.e., not in conflict) herewith.

Figure 2:
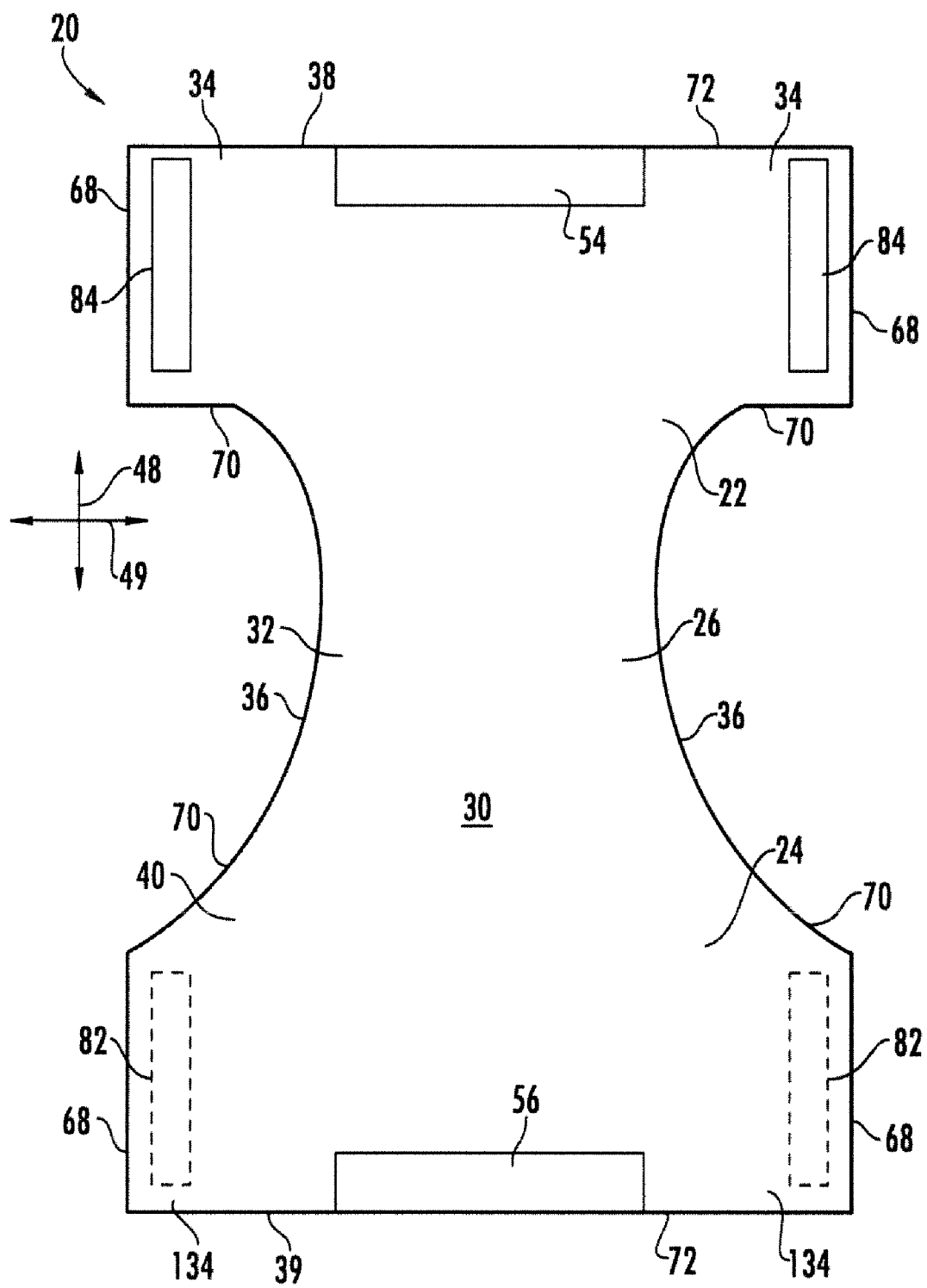
FIG. 2 is a plan view of the absorbent article shown in FIG. 1 with the article in an unfastened, unfolded and laid flat condition showing the surface of the article that faces away from the wearer.
Figure 3:
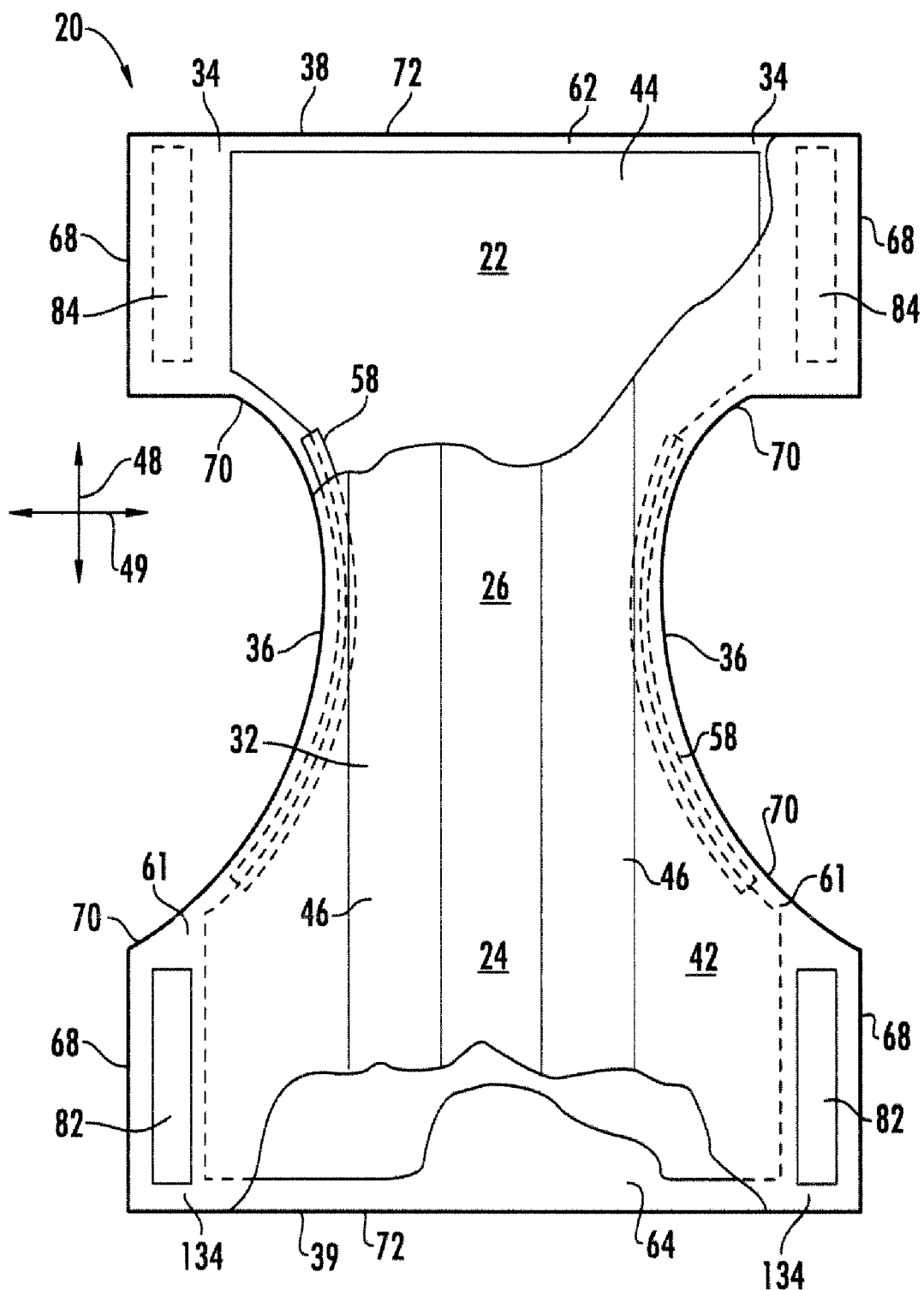
FIG. 3 is a plan view similar to FIG. 2 showing the surface of the absorbent article that faces the wearer when worn and with portions cut away to show underlying features.

A pair of training pants 20 is representatively illustrated in FIG. 1 in a partially fastened condition. The training pant 20 shown in FIG. 1 is also represented in FIGS. 2 and 3 in an opened and unfolded state. Specifically, FIG. 2 is a plan view illustrating the exterior side of the pants 20, while FIG. 3 illustrates the interior side of the pants 20. As shown in FIGS. 2 and 3, the pants 20 defines a longitudinal direction 48 (i.e., the machine direction) that extends from the front of the training pants when worn to the back of the training pants. Opposite to the longitudinal direction 48 is a lateral direction 49 (i.e., the cross-machine direction).

The pants 20 define a pair of longitudinal end regions, otherwise referred to herein as a front region 22 and a back region 24, and a center region, otherwise referred to herein as a crotch region 26, extending longitudinally between and interconnecting the front and back regions 22, 24. The pant 20 also defines an inner surface 28 adapted in use (e.g., positioned relative to the other components of the pants 20) to be disposed toward the wearer, and an outer surface 30 opposite the inner surface. The front and back regions 22, 24 are those portions of the pants 20, which when worn, wholly or partially cover or encircle the waist or mid-lower torso of the wearer. The crotch region 26 generally is that portion of the pants 20 which, when worn, is positioned between the legs of the wearer and covers the lower torso and crotch of the wearer.

The training pants 20 have a pair of laterally opposite side edges 36 and a pair of longitudinally opposite waist edges, respectively designated front waist edge 38 and back waist edge 39.

The illustrated pants 20 may include a chassis 32, a pair of laterally opposite front side panels 34 extending laterally outward at the front region 22 and a pair of laterally opposite back side panels 134 extending laterally outward at the back region 24.

Referring to FIGS. 1-3, the chassis 32 includes an outer cover 40 and a bodyside liner 42 (FIGS. 1 and 3) that may be joined to the outer cover 40 in a superimposed relation therewith by adhesives, ultrasonic bonds, thermal bonds or other conventional techniques. Referring to FIG. 3, the liner 42 may suitably be joined to the outer cover 40 along the perimeter of the chassis 32 to form a front waist seam 62 and a back waist seam 64. As shown in FIG. 3, the liner 42 may suitably be joined to the outer cover 40 to form a pair of side seams 61 in the front region 22 and the back region 24. The liner 42 can be generally adapted, i.e., positioned relative to the other components of the pants 20, to be disposed toward the wearer's skin during wear of the pants. The chassis 32 may further include an absorbent structure 44 particularly shown in FIG. 3 disposed between the outer cover 40 and the bodyside liner 42 for absorbing liquid body exudates exuded by the wearer, and may further include a pair of containment flaps 46 secured to the bodyside liner 42 for inhibiting the lateral flow of body exudates.

With the training pants 20 in the fastened position as partially illustrated in FIG. 1, the front and back side panels 34, 134 can be connected together by a fastening system 80 to define a three-dimensional pants configuration having a waist opening 50 and a pair of leg openings 52. The front and back side panels 34 and 134, upon wearing of the pants 20, thus include the portions of the training pants 20 which are positioned on the hips of the wearer. The waist edges 38 and 39 of the training pants 20 are configured to encircle the waist of the wearer and together define a waist opening 50 of the pants.

The elasticized containment flaps 46 as shown in FIG. 3 define a partially unattached edge which assumes an upright configuration in at least the crotch region 26 of the training pants 20 to form a seal against the wearer's body. The containment flaps 46 can extend longitudinally along the entire length of the chassis 32 or may extend only partially along the length of the chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pants 20 may also suitably include a front waist elastic member 54 (FIG. 1), a rear waist elastic member 56, and leg elastic members 58 (FIG. 3), as are known to those skilled in the art. The waist elastic members 54 and 56 can be operatively joined to the outer cover 40 and/or the bodyside liner 42 and can extend over part or all of the waist edges 38, 39. The leg elastic members 58 can be operatively joined to the outer cover 40 and/or the bodyside liner 42 and positioned in the crotch region 26 of the training pants 20.

The waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate. In one particular aspect, for example, the leg elastic members 58 may include a plurality of dry-spun coalesced multifilament spandex elastomeric threads sold under the trade name LYCRA and available from Invista, Wilmington, Del., U.S.A.

As shown in FIGS. 1 through 3, the side panels 34 and 134 can be formed as an integral portion of the chassis 32. For example, the side panels 34, 134 can include a generally wider portion of the outer cover 40, the bodyside liner 42, and/or other components of the chassis 32. As described above, the side panels 34 and 134 may be attached together using any suitable fastening system 80.

In the embodiments shown in the figures, the side panels 34 and 134 are releasably attachable. It should be understood, however, that in other embodiments the side panels 34 and 134 may be permanently joined together. For instance, the side panels may be made from a unitary piece of material. Alternatively, the side panels may be bonded together using ultrasonic bonding, thermal bonding or an adhesive. In this embodiment, the absorbent article is pulled over the legs when being worn.

In an alternative embodiment of the present invention, the side panels 34 and 134 may be separately attached to the chassis 32. For instance, the front side panels 34 can be permanently bonded to and extend transversely outward beyond the side margins of the chassis 32. Similarly, the back side panels 134 can be permanently bonded to and extend transversely outward beyond the side margins of the chassis 32 and the back region 24. The side panels 34 and 134 may be bonded to the chassis 32 using attachment means known to those skilled in the art such as adhesive, thermal or ultrasonic bonding.

The front and back side panels 34 and 134 each have a longitudinal outer edge 68, and a leg end edge 70 disposed toward the longitudinal center of the training pants 20, and waist end edges 72 disposed toward a longitudinal end of the training pants. The leg end edges 70 and the outer edges 68 of the side panels 34 and 134 form part of the pant side edges 36 of the training pants 20. The leg end edges 70 of the training pants 20 may be suitably curved and/or angled relative to the lateral direction 49 to provide a better fit around the wearer's legs. However, it is understood that only one of the leg end edges 70 may be curved or angled, such as the leg end edge of the back region 24, or alternatively, neither of the leg end edges may be curved or angled, without departing from the scope of the present invention. The waist end edges 72 generally extend in the lateral direction 49. The waist end edges 72 of the front side panels 34 form part of the front waist edge 38 of the training pants 20, and the waist end edges 72 of the back side panels 134 form part of the back waist edge 39 of the pants.

In configurations where the side panels 34, 134 are separately attached, the side panels may be provided by an elastic material capable of stretching at least in a direction generally parallel to the lateral direction 49 of the training pants 20. Suitable elastic materials, as well as one process of incorporating elastic side panels into training pants, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular aspects, the elastic material may include a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; European Patent Application No. EP 0 217 032 published on Apr. 8, 1987 in the name of Taylor et al.; and PCT application WO 01/88245 in the name of Welch et al.; all of which are incorporated herein by reference to the extent that they are consistent (i.e., not in conflict) herewith. Alternatively, the side panel material may include other woven or non-woven materials, such as those described later herein as being suitable for construction of the outer cover 40 and/or the bodyside liner 42; mechanically pre-strained composites; or stretchable but inelastic materials.

The fastening system 80 may include laterally opposite first fastening components 82 adapted for refastenable engagement to corresponding second fastening components 84. In one aspect, a front or outer surface of each of the fastening components 82, 84 includes a plurality of engaging elements. The engaging elements of the first fastening components 82 are adapted to repeatedly engage and disengage corresponding engaging elements of the second fastening components 84 to releasably secure the pants 20 in its three-dimensional configuration.

The fastening components 82, 84 may be any refastenable fasteners suitable for absorbent articles, such as adhesive fasteners, cohesive fasteners, mechanical fasteners, or the like. In particular aspects the fastening components include mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

In the illustrated aspect, the first fastening components 82 include loop fasteners and the second fastening components 84 include complementary hook fasteners. Alternatively, the first fastening components 82 may include hook fasteners and the second fastening components 84 may be complementary loop fasteners. In another aspect, the fastening components 82, 84 can be interlocking similar surface fasteners, or adhesive and cohesive fastening elements such as an adhesive fastener and an adhesive-receptive landing zone or material; or the like. Although the training pants 20 illustrated in FIG. 1 indicate the back side panels 134 overlapping the front side panels 34 upon connection thereto, which is convenient, the training pants 20 can also be configured so that the front side panels 34 overlap the back side panels 134 when connected. One skilled in the art will recognize that the shape, density and polymer composition of the hooks and loops may be selected to obtain the desired level of engagement between the fastening components 82, 84. Optionally, either one or both of the fastening components 82, 84 may be provided by one of the inner or outer surfaces 28 and 30 of the side panels 34 and 134. Suitable fastening systems are also disclosed in the previously incorporated PCT Patent Application WO 00/37009 published Jun. 29, 2000 by A. Fletcher et al. and the previously incorporated U.S. Pat. No. 6,645,190 issued Nov. 11, 2003 to Olson et al.

Figure 4:
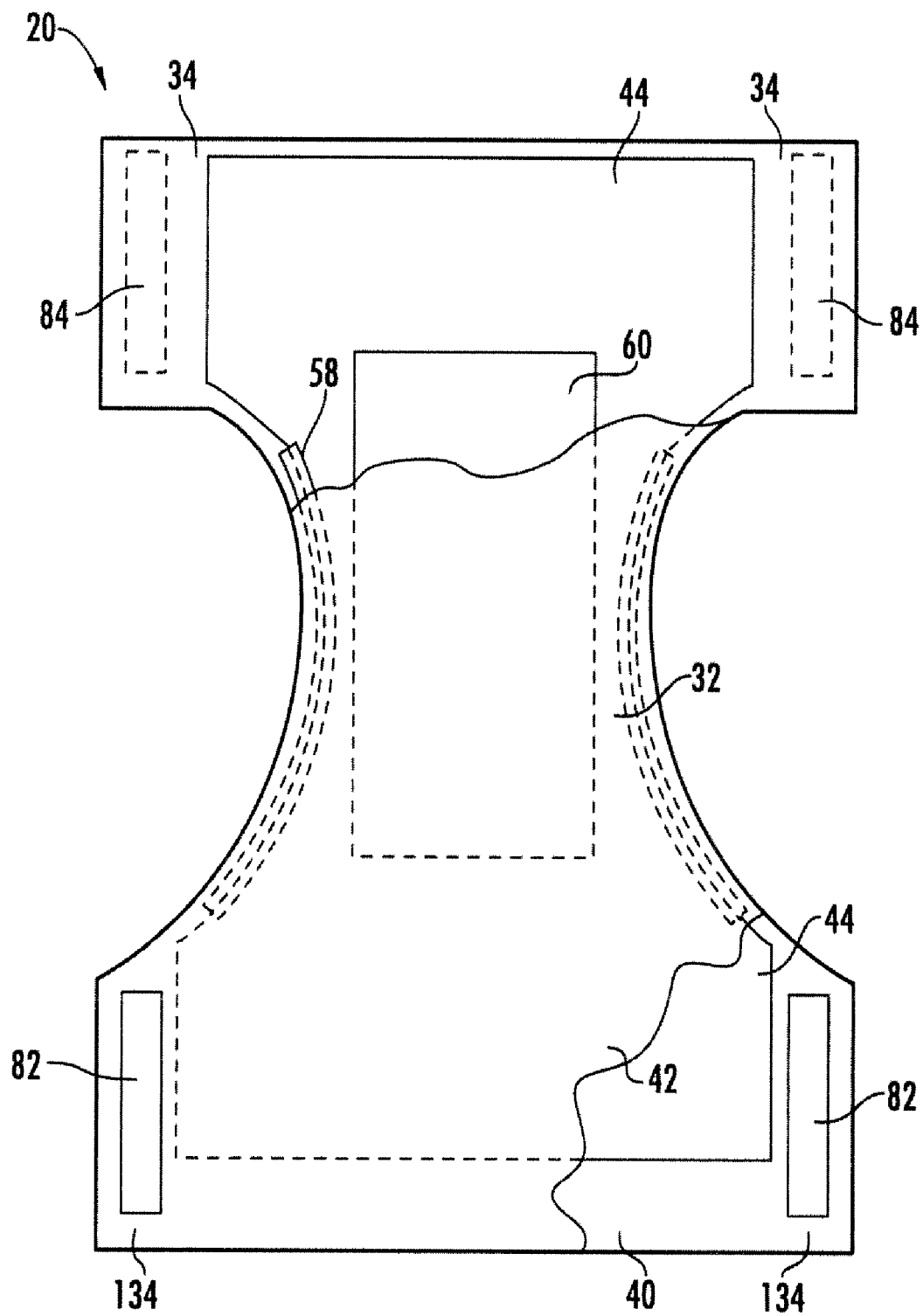
FIG. 4 is another embodiment of a plan view of an absorbent article made in accordance with the present invention showing the surface of the article that faces the wearer and with portions cut away to show underlying features.

Referring to FIG. 4, another embodiment of an absorbent article 20 made in accordance with the present invention is illustrated. In FIG. 4, the absorbent article 20 is shown in an unfolded state illustrating the interior surface of the article, which faces the wearer during use. In FIG. 4, the absorbent article 20 further includes a surge management layer 60 which may be optionally located adjacent the absorbent structure 44 and attached to various components in the article 20 such as the absorbent structure 44 or the bodyside liner 42 by methods known in the art, such as by using an adhesive. A surge management layer 60 helps to decelerate and diffuse surges or gushes of liquid that may be rapidly introduced into the absorbent structure of the article. Desirably, the surge management layer can rapidly accept and temporarily hold the liquid prior to releasing the liquid into the storage or retention portions of the absorbent structure. Examples of suitable surge management layers are described in U.S. Pat. No. 5,486,166; and U.S. Pat. No. 5,490,846. Other suitable surge management materials are described in U.S. Pat. No. 5,820,973. The entire disclosures of these patents are hereby incorporated by reference herein to the extent they are consistent (i.e., not in conflict) herewith.

I. Outer Cover

Figure 5:
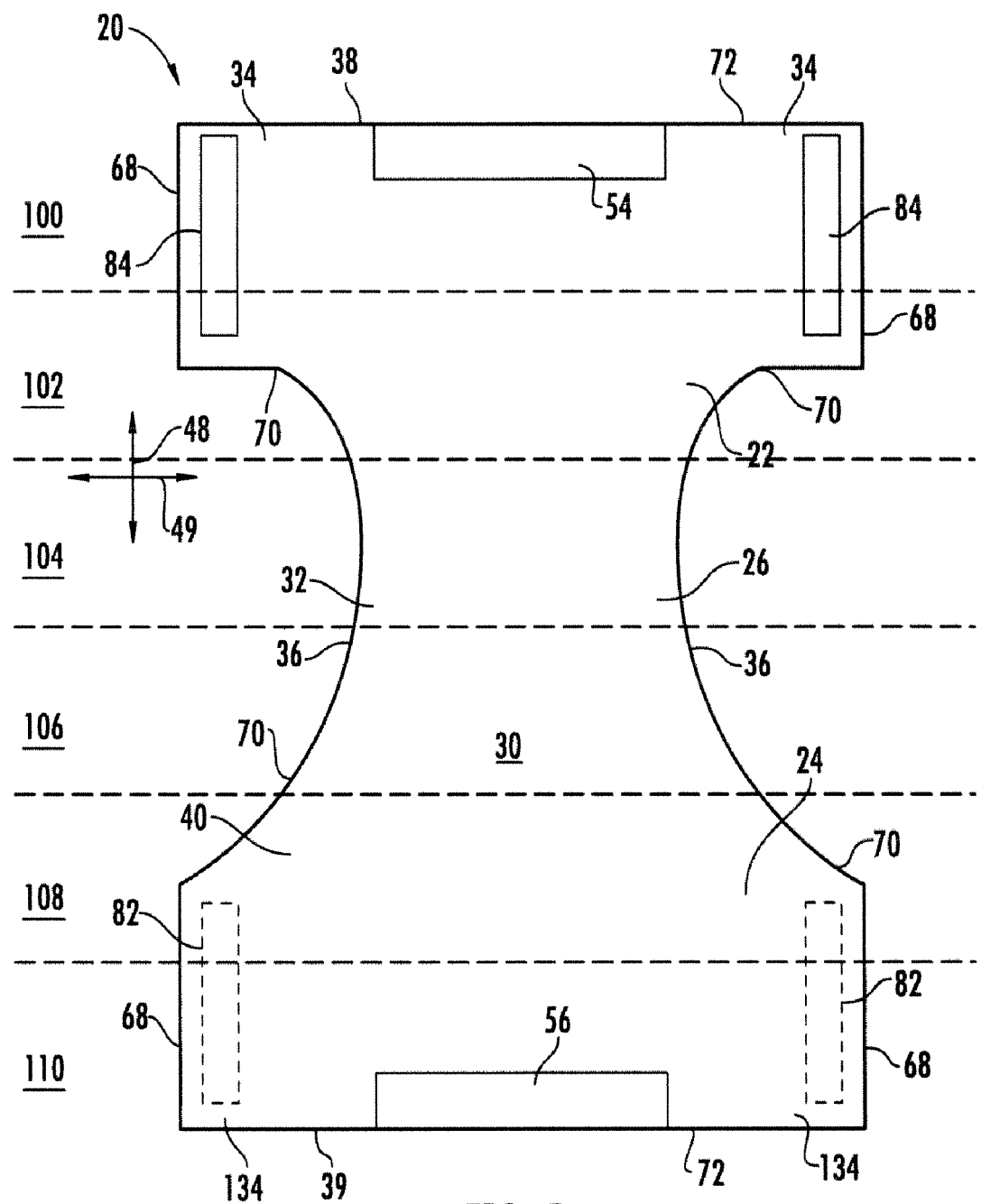
FIG. 5 is a plan view of the absorbent article shown in FIG. 2 illustrating the outer cover partitioned into 4 equidistant zones.
Figure 6:
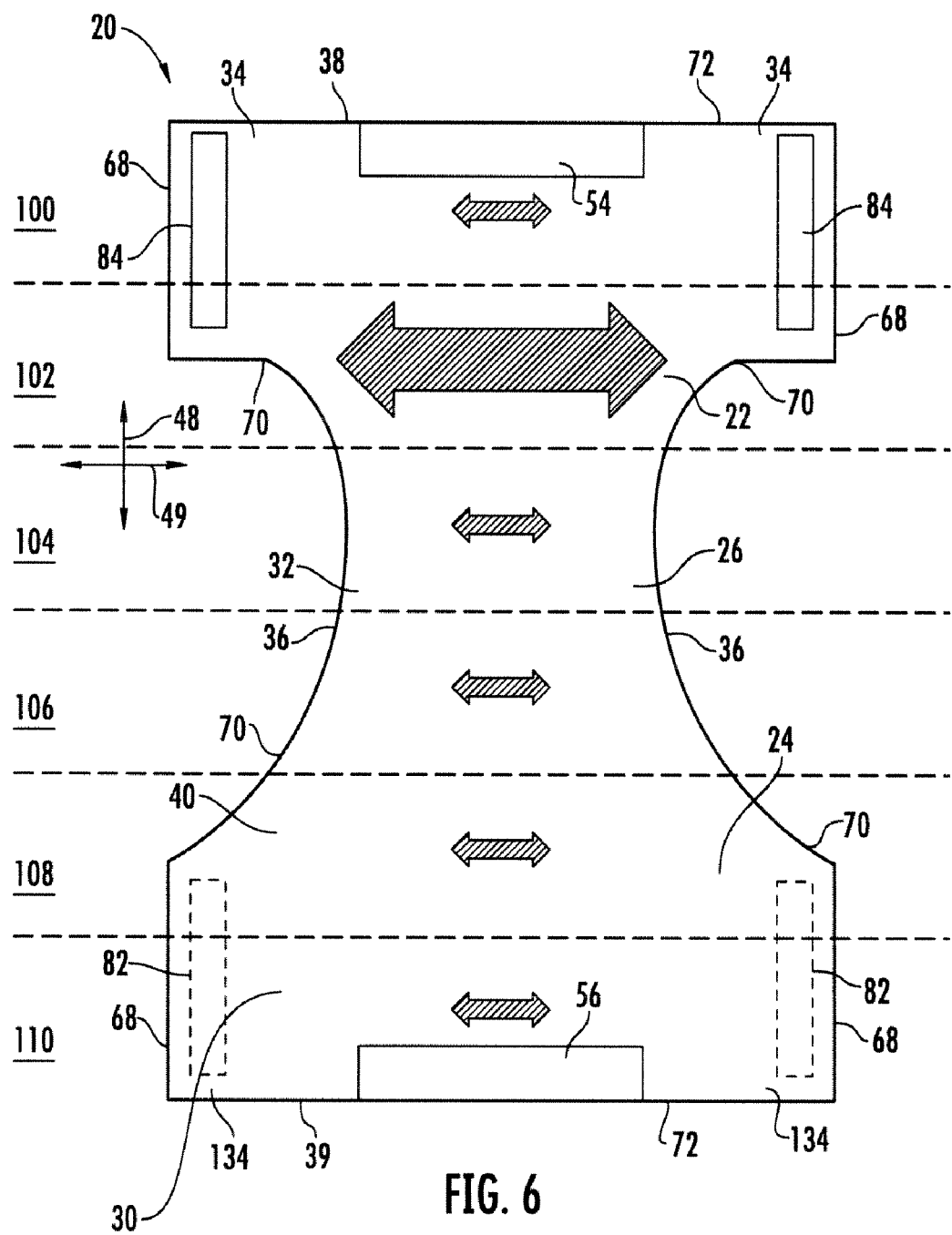
FIG. 6 is a plan view of the absorbent article shown in FIG. 5 illustrating the lateral stretch properties of the outer cover.

As described above, the present invention is particularly directed to an outer cover having controlled stretch properties. In particular, the tension in the front leg area of the outer cover can be controlled and decreased while the article is being worn. FIGS. 5 and 6 show the outer cover 40 partitioned into 6 equidistant zones for the purposes explanation: a front waist zone 100, a front leg zone 102, a front crotch zone 104, a back crotch zone 106, a back leg zone 108, and a back waist zone 110.

FIG. 6 shows the difference in the amount of lateral stretch available in the front leg zone 102 of the outer cover 40 compared to the front waist zone 100, the front crotch zone 104, the back crotch zone 106, the back leg zone 108, and the back waist zone 110 (not including the waist elastic members 54, 56 or the leg elastic members 58). For example, the front leg zone 102 of the outer cover 40 can have at least twice the amount of lateral stretch compared to the front waist zone 100, front crotch zone 104, the back crotch zone 106, the back leg zone 108, and/or the back waist zone 110, such as at least about three times the amount of stretch.

One method of measuring the amount of stretch in the outer cover 40 can be the stretch-to-stop method. "Stretch-to-stop" refers to a ratio determined from the difference between the unextended dimension of a stretchable laminate and the maximum extended dimension of a stretchable laminate upon the application of a specified tensioning force and dividing that difference by the unextended dimension of the stretchable laminate. If the stretch-to-stop is expressed in percent, this ratio is multiplied by 100. For example, a stretchable laminate having an unextended length of 5 inches (12.7 cm) and a maximum extended length of 10 inches (25.4 cm) upon applying a force of 2000 grams has a stretch-to-stop (at 2000 grams) of 100 percent. Stretch-to-stop may also be referred to as "maximum non-destructive elongation." Maximum non-destructive elongation would apply in the case of a material that has more than one perceived stretch-to-stop due to its construction. Unless specified otherwise, stretch-to-stop values are reported herein at a load of 2000 grams. In the case of more than one perceived stretch-to-stop, the load of the stretch-to-stop or maximum non-destructive elongation value may occur at less than 2000 grams. In the elongation or stretch-to-stop test, a 3-inch by 7-inch (7.62 cm by 17.78 cm) sample, with the larger dimension being the machine direction, the cross direction, or any direction in between, is placed in the jaws of a tensile tester, such as a Sintech tensile tester, manufactured by Sintech Inc., Research Triangle Park, N.C., using a gap of 5 cm between the jaws. The sample is then pulled to a stop load of 2000 gms with a crosshead speed of about 20 inches/minute (50.8 cm/minute).

For example, the front leg zone 102 of the outer cover 40 can have a stretch-to-stop at 2000 grams-force in the lateral direction 49 of from about 100% to about 250%, such as from about 125% to about 200%. Conversely, front waist zone 100, front crotch zone 104, the back crotch zone 106, back leg zone 108, and back waist zone 110 of the outer cover 40 can have a stretch-to-stop at 2000 grams-force in the lateral direction 49 of from about 50% to about 90%.

This increased amount of stretch available in the front leg zone 102 of the outer cover 40 can allow the front leg zone 102 to have less extension tension in the lateral direction 49 to relieve any tightness during wear in this front leg zone 102. Ideally, the front leg zone 102 has a tension of from about 300 grams-force to about 1200 grams-force, while the rest of the outer cover 40 can have a tension of from about up to about 1500 grams-force, when stretched to 160% to 175% of its unstretched length in the lateral direction 49, which can also be measured using the tensile tester described above. For example, when stretched to the 160% to 175% of its length in the lateral direction 49, the tension in the front waist zone 100, the front crotch zone 104, the back crotch zone 106, the back leg zone 108, and the back waist zone 110 of the outer cover 40 can be from about 1500 grams-force to about 2500 grams-force, while the tension in the front leg zone 102 of the outer cover 40 can be from about 300 grams-force to about 1000 grams-force.

It should be understood that the above stretch properties of absorbent articles made in accordance with the present invention are contained in the outer cover 40 in the lateral direction 49. As used herein, the stretch properties are independent of the properties of any auxiliary components, such as flap elastics, elastic gasket components, or leg elastic components.

Through the above construction, the absorbent article 20 is provided with form-fitting properties that not only maximize comfort but also provide an aesthetically pleasing appearance when worn. The ability of the front leg zone 102 of the outer cover 40 to handle increased tension forces exerted on it in the lateral direction, compared to the other zones of the outer cover 40, can allow for an improved fit in the article and thus better fluid handling. Further, the stretch properties facilitate donning of the article.

Various techniques may be used in order to produce the absorbent article 20 with the above stretch properties. In constructing absorbent articles in accordance with the present invention, for instance, the outer cover 40 may be elastic, while the bodyside liner 42 is stretchable or vice versus. In other embodiments, both the outer cover and the bodyside liner may be elastic. Depending upon the construction of the article, the absorbent structure 44 may also be stretchable and/or elastic.

In one particular embodiment, the outer cover 40 is made from stretchable and/or elastic materials.

The outer cover 40 may be made from various materials. The outer cover 40, for instance, may be breathable and/or may be liquid impermeable. The outer cover 40 may be constructed of a single layer, multiple layers, laminates, spunbond fabrics, films, meltblown fabrics, elastic netting, microporous webs, bonded card webs or foams provided by elastomeric or polymeric materials. The outer cover 40, for instance, can be a single layer of a liquid impermeable material, or alternatively can be a multi-layered laminate structure in which at least one of the layers is liquid impermeable. In other embodiments, however, it should be understood that the outer cover may be liquid permeable. In this embodiment, for instance, the absorbent article may contain an interior liquid barrier layer.

For instance, the outer cover 40 can include a liquid permeable outer layer and a liquid impermeable inner layer that are suitably joined together by a laminate adhesive, ultrasonic bonds, thermal bonds, or the like. Suitable laminate adhesives, which can be applied continuously or intermittently as beads, a spray, parallel swirls, or the like, can be obtained from Bostik Findley Adhesives, Inc., of Wauwatosa, Wis., U.S.A., or from National Starch and Chemical Company, Bridgewater, N.J. U.S.A. The liquid permeable outer layer can be any suitable material and is desirably one that provides a generally cloth-like texture. One example of such a material is a 20 gsm (grams per square meter) spunbond polypropylene nonwoven web. The outer layer may also be made of those materials of which the liquid permeable bodyside liner 42 is made.

The inner layer of the outer cover 40 can be both liquid and vapor impermeable, or it may be liquid impermeable and vapor permeable. The inner layer can be manufactured from a thin plastic film, although other flexible liquid impermeable materials may also be used. The inner layer, or the liquid impermeable outer cover 40 when a single layer, prevents waste material from wetting articles, such as bed sheets and clothing, as well as the wearer and caregiver. A suitable liquid impermeable film for use as a liquid impermeable inner layer, or a single layer liquid impermeable outer cover 40, is a 0.02 millimeter polyethylene film commercially available from Pliant Corporation of Schaumburg, Ill., U.S.A.

In most embodiments, the outer cover 40 is stretchable and optionally elastic. Elastic non-woven laminate webs that can be used as the outer cover 40 include a non-woven material joined to one or more gatherable non-woven webs, films, or foams. Stretch Bonded Laminates (SBL) and Neck Bonded Laminates (NBL) are examples of elastomeric composites. Non-woven fabrics are any web of material which has been formed without the use of textile weaving processes which produce a structure of individual fibers that are interconnected in an integrating manner.

Examples of suitable materials are spunbond-meltblown fabrics, spunbond-meltblown-spunbond fabrics, spunbond fabrics, or laminates of such fabrics with films, foams, or other nonwoven webs. Elastomeric materials may include cast or blown films, foams, meltblown fabrics or spunbond fabrics composed of polyethylene, polypropylene, or polyolefin elastomers, as well as combinations thereof. The elastomeric materials may include PEBAX elastomer (available from AtoChem located in Philadelphia, Pa.), HYTREL elastomeric polyester (available from Invista of Wilmington, Del.), KRATON elastomer (available from Kraton Polymers of Houston, Tex.), or strands of LYCRA elastomer (available from Invista of Wilmington, Del.), or the like, as well as combinations thereof. The outer cover 40 may include materials that have elastomeric properties through a mechanical process, printing process, heating process, or chemical treatment. For examples such materials may be apertured, creped, neck-stretched, heat activated, embossed, and micro-strained; and may be in the form of films, webs, and laminates.

In particular aspects of the invention, the outer cover 40 may include a 0.4 ounces per square yard (osy) (13.6 grams per square meter (gsm)) basis weight layer of G2760 KRATON elastomer strands adhesively laminated with a 0.3 gsm layer of adhesive between two facings. Each facing can be composed of a thermal point bonded bicomponent spunbond non-woven fibrous web having a 0.7 osy (23.7 gsm) basis weight. The adhesive is similar to an adhesive which is supplied by Bostik Findley Adhesive and designated as H2525A, and the elastomer strands are placed and distributed to provide approximately 12 strands of KRATON elastomer per inch (2.54 cm) of lateral width of the outer cover 40.

Alternatively, the outer cover 40 may include a woven or non-woven fibrous web layer which has been totally or partially constructed or treated to impart the desired levels of liquid impermeability to selected regions that are adjacent or proximate the absorbent structure. For example, the outer cover 40 may include a gas-permeable, non-woven fabric layer laminated to a polymer film layer which may or may not be gas-permeable. Other examples of fibrous, cloth-like outer cover 40 materials can include a stretch thinned or stretch thermal laminate material composed of a 0.6 mil (0.015 mm) thick polypropylene blown film and a 0.7 osy (23.8 gsm) polypropylene spunbond material (2 denier fibers).

Suitable materials for a biaxially stretchable outer cover 40 include biaxially stretchable material and biaxially elastic stretchable material. One example of a suitable outer cover material can include a 0.3 osy (10.2 gsm) polypropylene spunbond that is necked 60% in the lateral direction 49 and creped 60% in the longitudinal direction 48, laminated with 3 grams per square meter (gsm) Findley 2525A styrene-isoprene-styrene based adhesive to 8 gsm PEBAX 2533 film with 20% $TiO_2$ concentrate.

Another example of a suitable material for a biaxially stretchable outer cover 40 is a breathable elastic film/non-woven laminate, described in U.S. Pat. No. 5,883,028, issued to Morman et al., incorporated herein by reference to the extent that it is consistent (i.e. not in conflict) herewith. Examples of materials having two-way stretchability and retractability are disclosed in U.S. Pat. No. 5,116,662 issued to Morman and U.S. Pat. No. 5,114,781 issued to Morman, both of which are hereby incorporated herein by reference to the extent that it is consistent (i.e., not in conflict) herewith. These two patents describe composite elastic materials capable of stretching in at least two directions. The materials have at least one elastic sheet and at least one necked material, or reversibly necked material, joined to the elastic sheet at least at three locations arranged in a nonlinear configuration, so that the necked, or reversibly necked, web is gathered between at least two of those locations.

A. Control of the Stretch Properties by Altering the Outer Cover

One particular embodiment of the present invention involves weakening the outer cover 40 in the front leg zone 102 to increase the ability of this area of the outer cover 40 to be stretched (e.g., less tension can be present in the front leg zone 102 at the same amount of lateral stretch than in the other zones). The front leg zone 102 can also expand and/or stretch more than the other zones of the outer cover 40 under the same amount of force. This increased stretching can lead to decreased tension in the front leg zone 102 of the outer cover 40.

Figure 7:
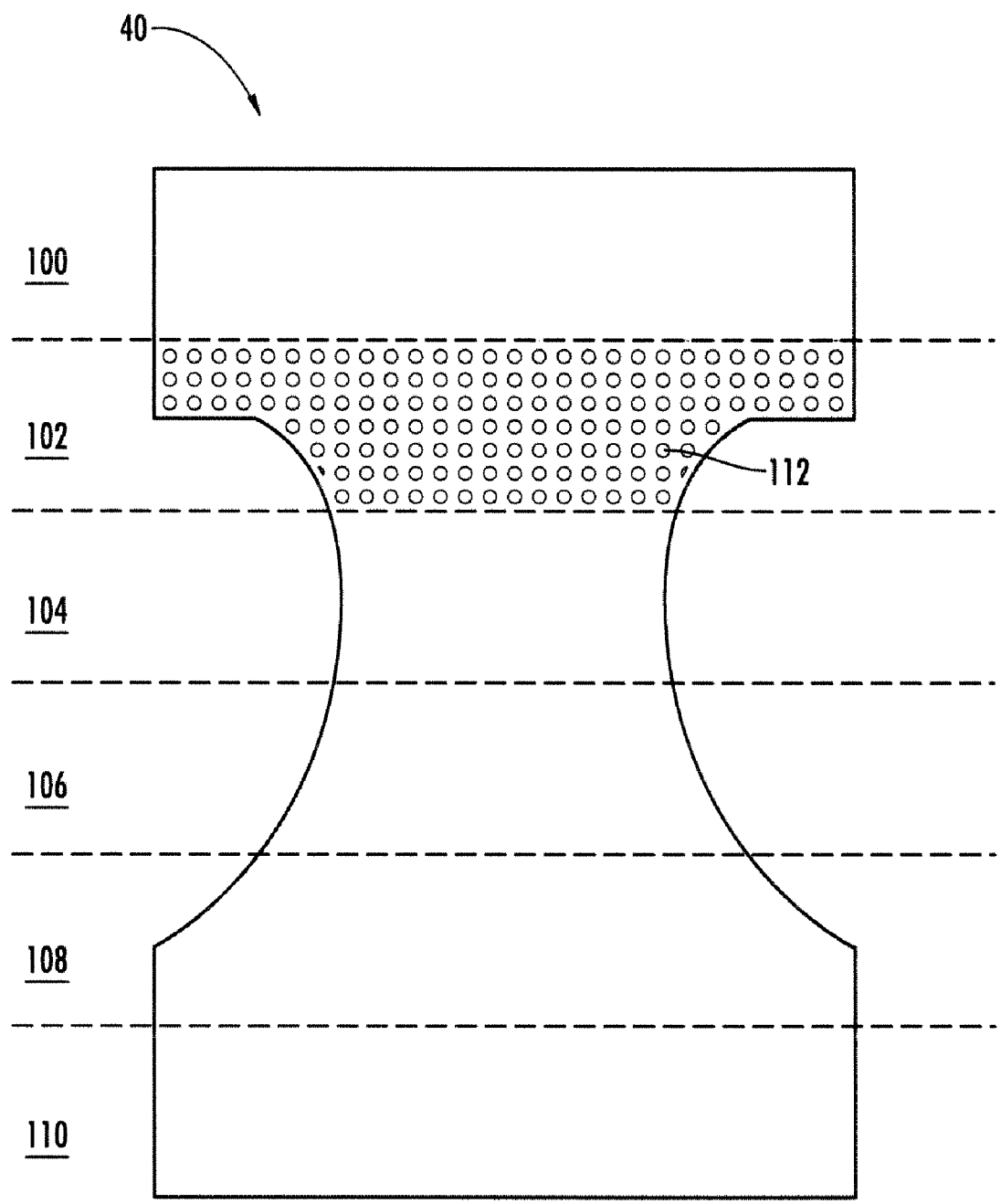
FIGS. 7, 7A, 7B, and 7C are plan views of other exemplary outer covers having apertures or slits in the front leg zone for use in the absorbent article shown in FIGS. 5 and 6.

FIG. 7 shows the outer cover 40 having small apertures 112 located within the front leg zone 102. These apertures 112 weaken the front leg zone 102 of the apertures 112 to allow for greater stretching of the outer cover 40 upon donning. Thus, the tension in the front leg zone 102 can be reduced (when compared to an otherwise identical non-apertured outer cover) upon donning of the training pants 20.

The size, shape, and quantity of the apertures 112 can vary as desired to control the amount of weakening of the outer cover 40 in the front leg zone 102. For example, the shape of the apertures 112 can be circular, oval, square, rectangular, or any other shape. In one particular embodiment, the apertures 112 can be slits that are essentially liner cuts in the outer cover 40. These slits can be oriented in the longitudinal direction 48, the lateral direction 49, or in a direction therebetween.

The size of the apertures 112 can be small slits (e.g., linear cuts) that have length of about 1 mm to about 20 mm, such as from about 2 mm to about 10 mm. When circular under substantially no stretching force in any direction, the apertures can have a diameter of, for example, from about 0.1 mm (i.e., essentially a pin-hole) to about 5 mm, such as from about 0.2 mm to about 3 mm.

Figure 7A:
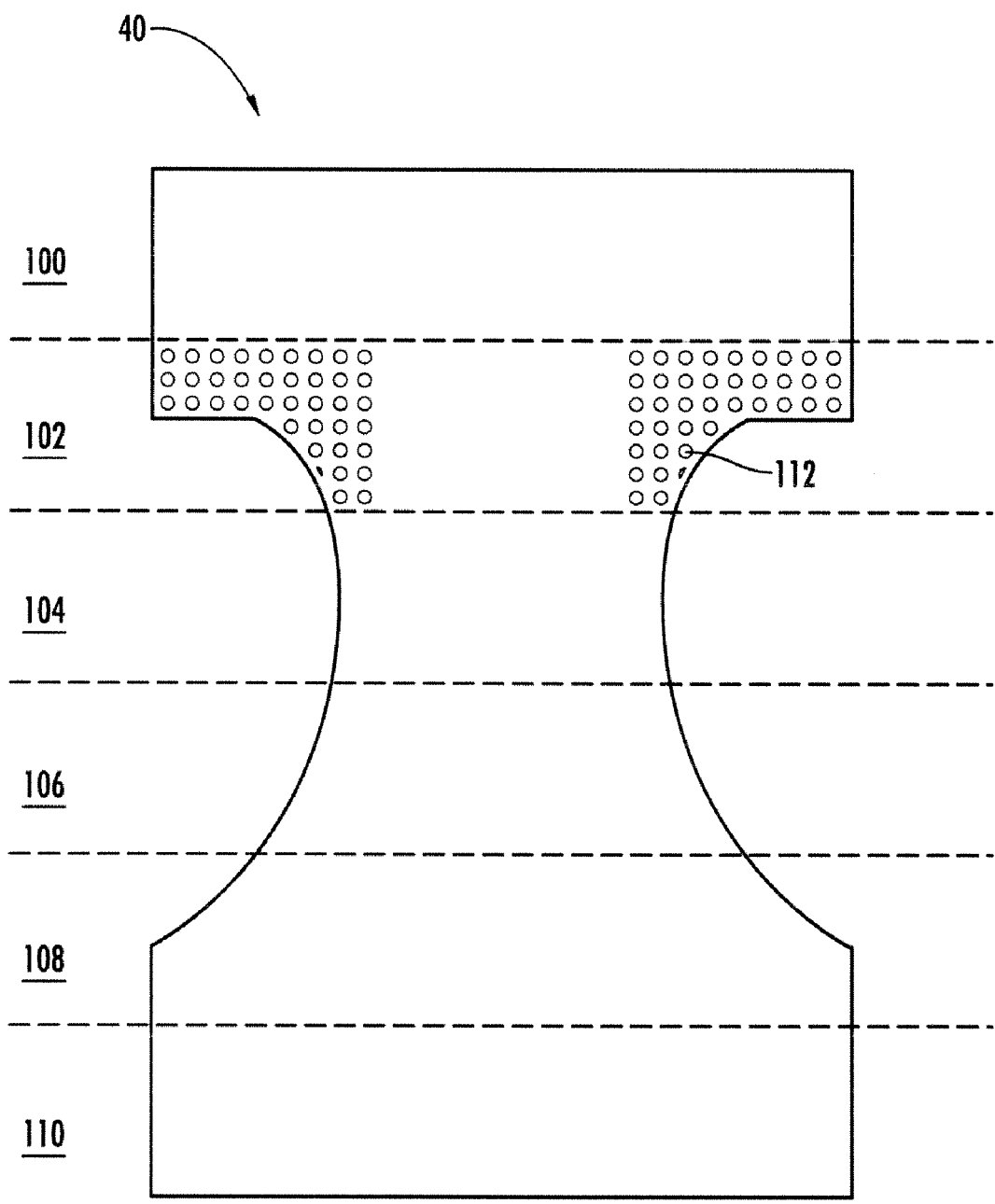

Although the apertures 112 are shown substantially uniformly distributed throughout the front leg zone 102 in FIG. 7, the apertures 112 can be non-uniformly distributed in the front leg zone 102. In one particular embodiment, the apertures 112 can be formed along the side edges of the front leg zone 102, leaving the center portion of the front leg zone 102 substantially free of any apertures 112, as shown in FIG. 7A. Not wishing to be bound by theory, it is believed that a majority of the lateral stretch of the outer cover 40 in the front leg zone 102 occurs along the side edges not the center portion of this zone during wear. Thus, this positioning of apertures 112 along the side edges can allow for greater stretch in the areas where the tension forces are expected during wear. For explanation purposes, the front leg zone 102 of the outer cover 40 can be further divided into 3 equidistant sections in the lateral direction 49: the two side edge sections and a center section. The apertures 112 can be, in one embodiment, present only in the two side sections, and absent from the center section.

Figure 7B:
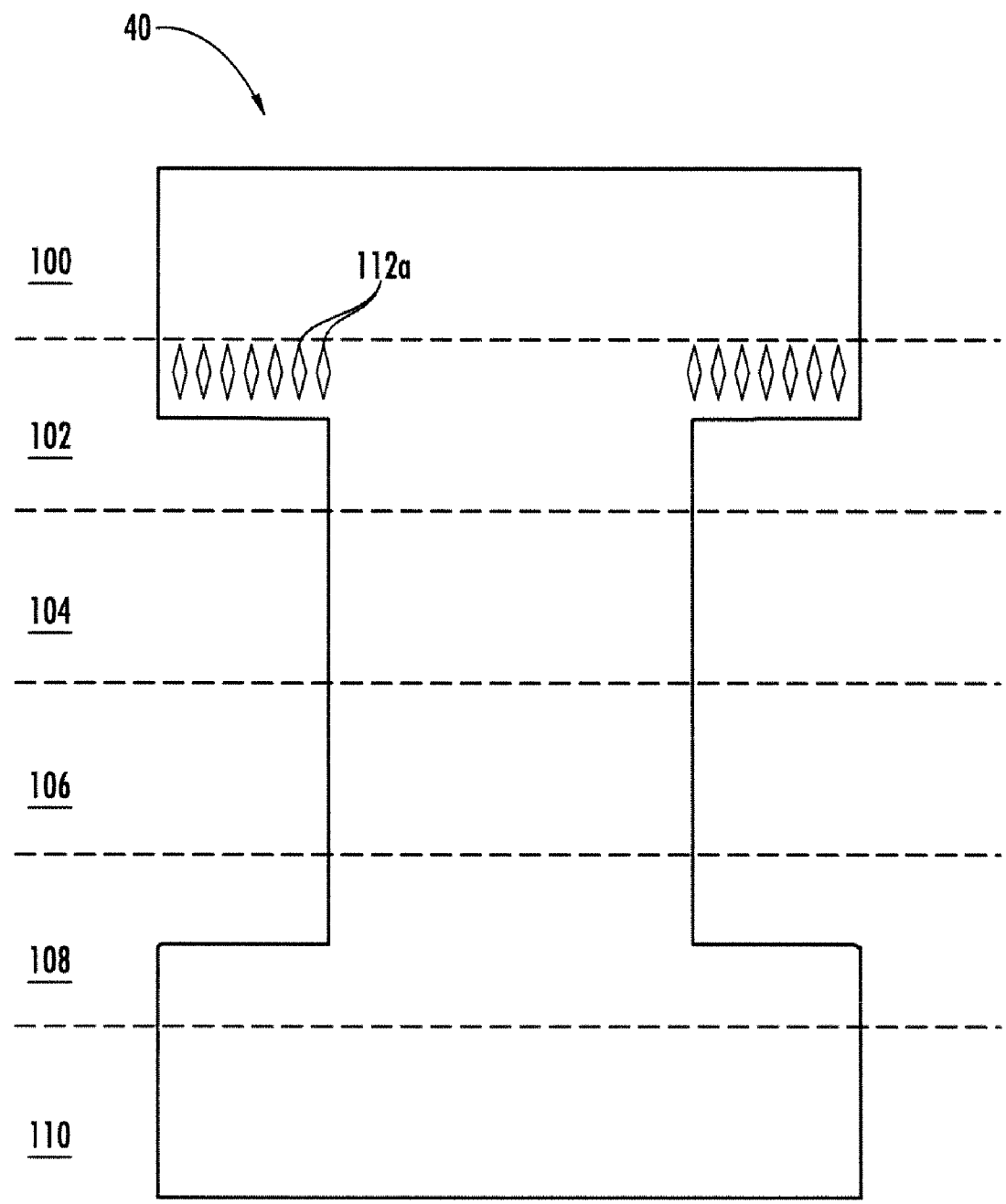
Figure 7C:
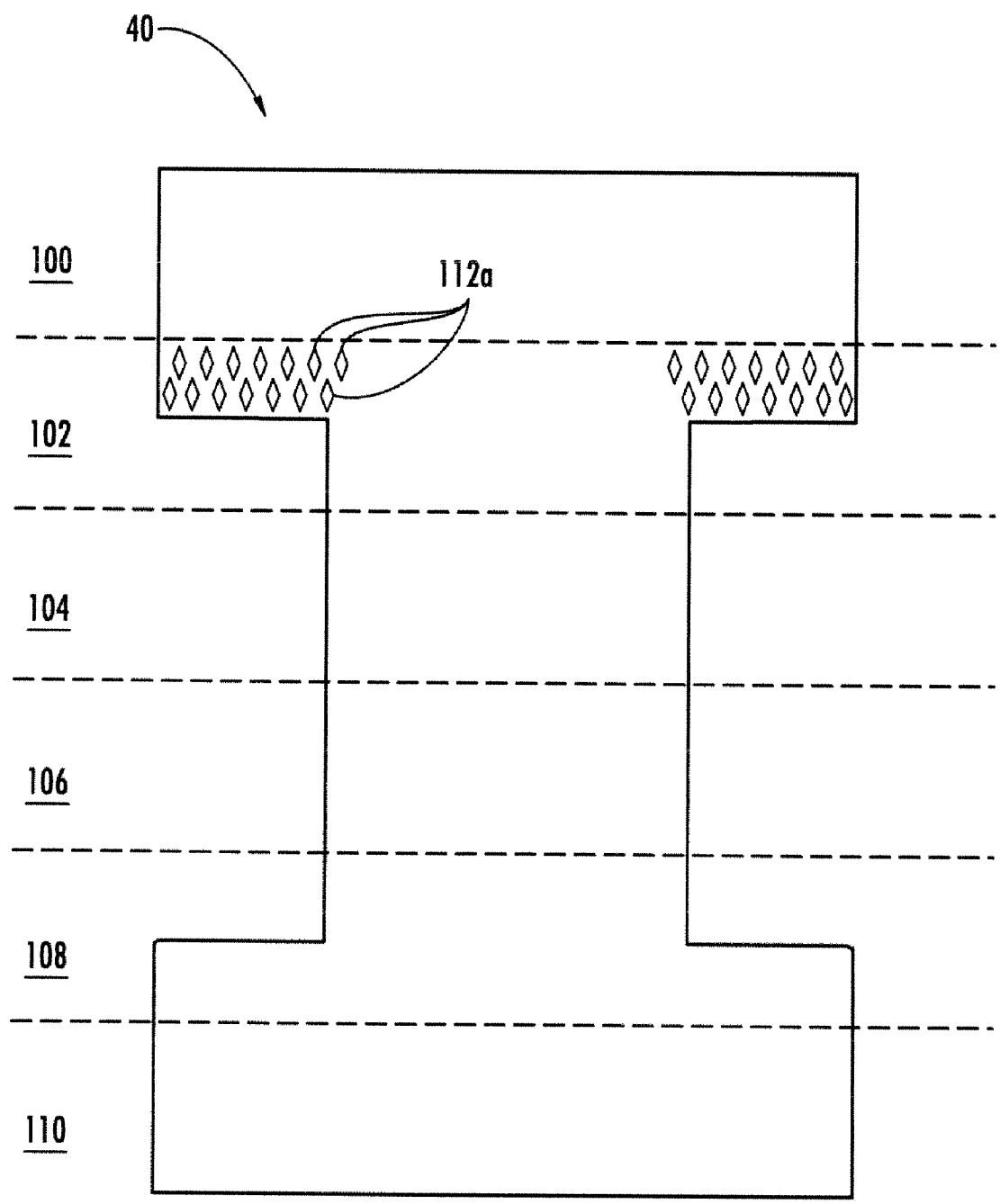

Other particular embodiments are shown in FIGS. 7B and 7C. These embodiments have diamond shaped slits 112a in the front leg zone 102 of the outer cover 40. These diamond shaped slits 112a are generally narrow in the lateral direction 49 and long in the longitudinal direction 48. For example, the diamond shaped slits 112a can be have a length in the longitudinal direction 48 that is at least twice as long as a width in the lateral direction 49, such as from about 3 times as long to about 50 times as long, when under no stretching tension. Put another way, the ratio of the length in the longitudinal direction 48 to the width in the lateral direction 49 of the diamond shaped slits 112a can be greater than 2:1, such as from about 3:1 to about 50:1, when no stretching force is applied to the outer cover 40. The narrow shape of the diamond shaped slits 112a allows the diamond shaped slits 112a to spread apart in the lateral direction 49 to open to a wide diamond shaped slit from a narrow diamond shaped slit when subjected to a stretching force in the lateral direction 49.

The diamond shaped slits 112a can be positioned throughout the front leg zone 102 or can be positioned in certain areas. For example, FIGS. 7B and 7C show that the diamond shaped slits 112a are positioned in the two side sections and are absent from the center section.

The diamond shaped slits 112a are also particularly useful when the outer cover 40 has substantially right angles (i.e., about 90°) defining the transition from the waist portion to the leg opening, as shown in FIGS. 7B and 7C.

Figure 8:
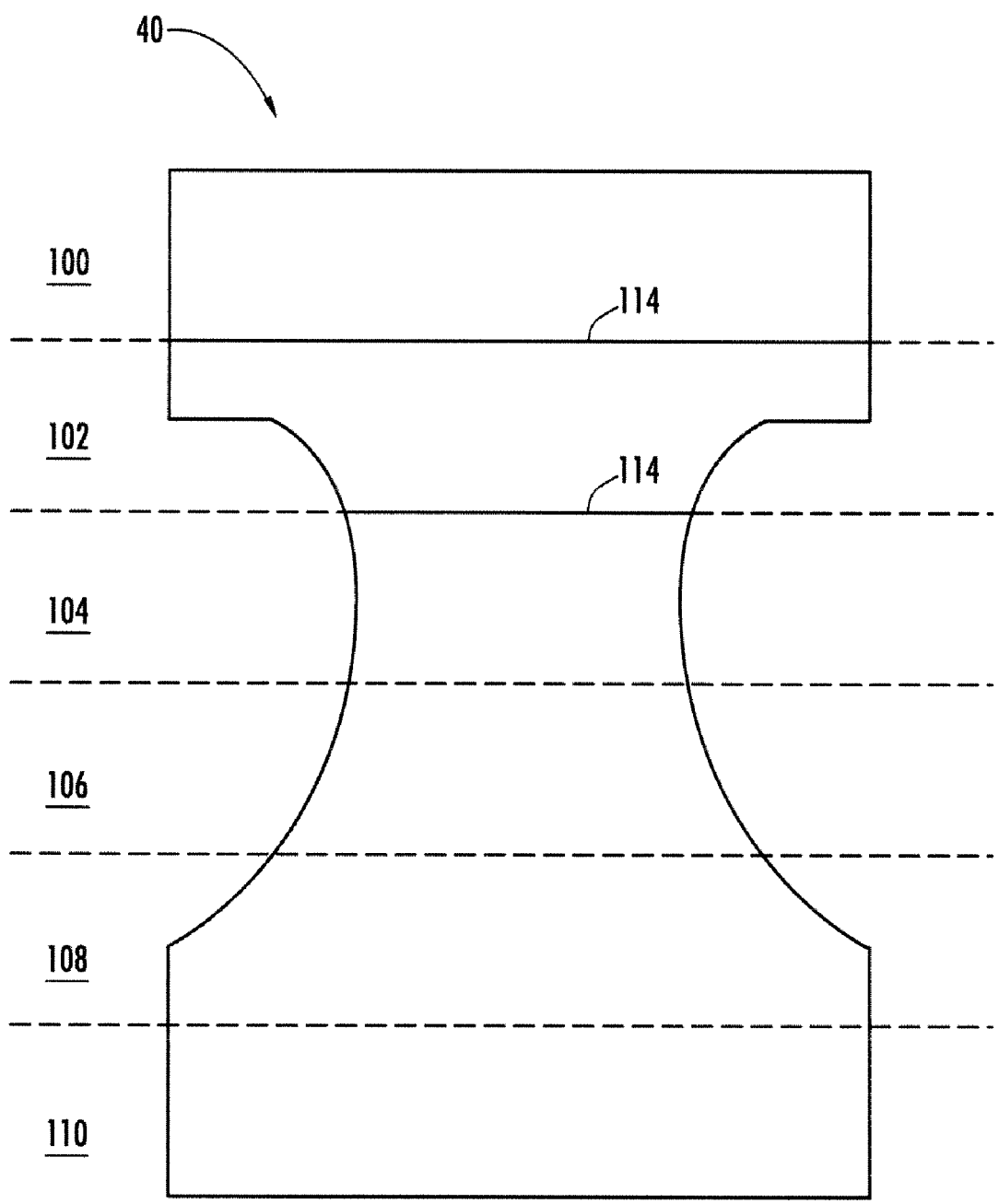
FIG. 8 is a plan view of another exemplary outer cover assembled from three pieces for use in the absorbent article shown in FIGS. 5 and 6.

The diamond shaped slits 112a can be arranged in a row across the front leg zone 102 (or portion thereof) or can be arranged in multiple rows. FIG. 8 shows the diamond shaped slits 112a positioned in two rows such that the individual diamond shaped slits 112a alternate in an offset manner across each of the side sections of the front leg zone 102.

The apertures 112 can be formed using a perforation roll, a laser, an ultrasonic horn, a knife, or any other device, as is known in the art.

For example, in one embodiment, a roll having a plurality of pins extending from its surface can be utilized to perforate the front leg zone 102 of the outer cover 40. The perforated or grooved roll can be timed or have relieved areas so as to avoid cutting or otherwise altering the front waist zone 100, the front crotch zone 104, back crotch zone 106, back leg zone 108, and back waist zone 110.

B. Control of Stretch Properties Through a Multi-Piece Outer Cover

In another alternative embodiment of the present invention, the outer cover 40 may be formed from multiple components and separate pieces that are attached together to form the outer cover 40 having the desired stretch properties. In this embodiment, for instance, the outer cover 40 may be made from three separate pieces of material. Two pieces of material may be used, for instance, to construct the front waist zone 100 and, collectively, the front crotch zone 104, the back crotch zone 106, the back leg zone 108, and the back waist zone 110. These pieces of material may be stretchable and/or elastic. The front leg zone 102 of the outer cover 40, however, may be made from a material that has higher stretch properties than the material used to form the other zones. The three pieces of material may then be connected or attached together using any suitable attachment technique, such as thermal bonding or through the use of an adhesive. In this embodiment, the liner may also be made from three separate pieces of material that assist in matching the stretch characteristics of the outer cover 40.

FIG. 8 shows an exemplary outer cover constructed from three pieces, each connected to each other at seam 114.

C. Control of the Stretch Properties with an Adhesive

In accordance with the present invention, an adhesive may be applied in order to tailor the stretch properties of the outer cover 40 to a particular application. For instance, the adhesive may be applied in a pattern to allow for greater stretch in the front leg zone 102. In this embodiment, heavy amounts of adhesive can be positioned in the front waist zone 100, the front crotch zone 104, the back crotch zone 106, the back leg zone 108, and the back waist zone 110 while lesser amounts of adhesive (or no adhesive) is applied in the front leg zone 102. In this manner, the front waist zone 100, front crotch zone 104, the back crotch zone 106, the back leg zone 108, and the back waist zone 110 have less stretch properties than the front leg zone 102. As one skilled in the art may appreciate, however, the adhesive may be applied in other patterns for further altering the overall stretch properties of the product.

The adhesive used to construct the absorbent article 20 may be any suitable adhesive for the application. For instance, in one embodiment, a hot melt adhesive may be used. In addition to using an adhesive, various other attachment devices may be used in order to alter the stretch properties of the outer cover. For instance, in other embodiments, the absorbent structure may be ultrasonically bonded to the chassis 32, thermally bonded to the chassis 32, or bonded using heat crimping. In other embodiments, a mechanical attachment structure such as a hook and loop fastening system may be used in order to secure the absorbent structure to the chassis.

II. Bodyside Liner

The bodyside liner 42 is suitably compliant, soft-feeling, and non-irritating to the wearer's skin. The bodyside liner 42 is also sufficiently liquid permeable to permit liquid body exudates to readily penetrate through its thickness to the absorbent structure 44. A suitable bodyside liner 42 may be manufactured from a wide selection of web materials, such as porous foams, reticulated foams, apertured plastic films, woven and non-woven webs, or a combination of any such materials. For example, the bodyside liner 42 may include a meltblown web, a spunbonded web, or a bonded-carded-web composed of natural fibers, synthetic fibers or combinations thereof. The bodyside liner 42 may be composed of a substantially hydrophobic material, and the hydrophobic material may optionally be treated with a surfactant or otherwise processed to impart a desired level of wettability and hydrophilicity.

The bodyside liner 42 may also be stretchable, and more suitably it may be elastomeric. Suitable elastomeric materials for construction of the bodyside liner 42 can include elastic strands, LYCRA elastics, cast or blown elastic films, non-woven elastic webs, meltblown or spunbond elastomeric fibrous webs, as well as combinations thereof. Examples of suitable elastomeric materials include KRATON elastomers, HYTREL elastomers, ESTANE elastomeric polyurethanes (available from Noveon of Cleveland, Ohio), or PEBAX elastomers.

As an additional example, in one aspect the bodyside liner 42 suitably includes a non-woven, spunbond polypropylene fabric composed of about 2 to 3 denier fibers formed into a web having a basis weight of about 12 gsm which is necked approximately 60 percent. Strands of about 9 gsm KRATON G2760 elastomer material placed eight strands per inch (2.54 cm) are adhered to the necked spunbond material. The fabric is surface treated with an operative amount of surfactant, such as about 0.6 percent AHCOVEL Base N62 surfactant, available from ICI Americas, a business having offices in Wilmington, Del., U.S.A. The surfactant can be applied by any conventional means, such as spraying, printing, brush coating or the like. Other suitable materials may be extensible biaxially stretchable materials, such as a neck stretched/creped spunbond. The bodyside liner 42 can also be made from extensible materials as are described in U.S. patent application Ser. No. 09/563,417 filed on May 3, 2000 by Roessler et al. The bodyside liner 42 can also be made from biaxially stretchable materials as are described in U.S. patent application Ser. No. 09/698,512 filed on Oct. 27, 2000 by Vukos et al.

III. Absorbent Structure

The absorbent structure 44 may be disposed between the outer cover 40 and the bodyside liner 42. The absorbent structure 44 can be any structure or combination of components which are generally compressible, conformable, non-irritating to a wearer's skin, and capable of absorbing and retaining liquids and certain body wastes. For example, the absorbent structure 44 may include an absorbent web material of cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In a particular aspect, the absorbent web material is a matrix of cellulosic fluff and superabsorbent hydrogel-forming particles. The cellulosic fluff may include a blend of wood pulp fluff. One preferred type of fluff is identified with the trade designation CR 1654, available from Bowater of Greenville, S.C., USA, and is a bleached, highly absorbent sulfate wood pulp containing primarily southern soft wood fibers. The absorbent materials may be formed into a web structure by employing various conventional methods and techniques. For example, the absorbent web may be formed with a dry-forming technique, an air forming technique, a wet-forming technique, a foam-forming technique, or the like, as well as combinations thereof. Methods and apparatus for carrying out such techniques are well known in the art. Furthermore, the absorbent structure may itself encompass multiple layers in the Z direction. Such multiple layers may take advantage of differences in absorbency capacity, such as by placing a lower capacity absorbent material layer closer to the liner 42 and a higher capacity absorbent material closer to the outer cover 40. Likewise, discrete portions of an absorbent single-layered structure may encompass higher capacity absorbents, and other discrete portions of the structure may encompass lower capacity absorbents.

As a general rule, the superabsorbent material is present in the absorbent web in an amount of from about 0 to about 90 weight percent based on total weight of the web. The web may have a density within the range of about 0.10 to about 0.60 grams per cubic centimeter.

Superabsorbent materials are well known in the art and can be selected from natural, synthetic, and modified natural polymers and materials. The superabsorbent materials can be inorganic materials, such as silica gels, or organic compounds, such as crosslinked polymers. Typically, a superabsorbent material is capable of absorbing at least about 10 times its weight in liquid, and desirably is capable of absorbing more than about 25 times its weight in liquid. Suitable superabsorbent materials are readily available from various suppliers. For example, SXM 9394, and Favor 9543 superabsorbents are available from DeGussa Superabsorbers.

After being formed or cut into a desired shape, the absorbent web material may be wrapped or encompassed by a suitable tissue or meltblown web or the like wrap sheet that aids in maintaining the integrity and shape of the absorbent structure 44.

The absorbent web material may also be a coform material. The term "coform material" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Any of a variety of synthetic polymers may be utilized as the melt-spun component of the coform material. For instance, in certain aspects, thermoplastic polymers can be utilized. Some examples of suitable thermoplastics that can be utilized include polyolefins, such as polyethylene, polypropylene, polybutylene and the like; polyamides; and polyesters. In one aspect, the thermoplastic polymer is polypropylene. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein by reference to the extent they are consistent (i.e., not in conflict) herewith.

In a particular aspect of the absorbent article of the present invention, the absorbent structure 44 may also be elastomeric. For this purpose, the absorbent web material can include elastomeric fibers in an amount which is at least a minimum of about 2 wt %. The amount of elastomeric fibers can alternatively be at least about 3 wt %, and can optionally be at least about 5 wt % to provide improved performance. In addition, the amount of elastomeric fibers can be not more than about 60 wt %. Alternatively, the amount of elastomeric fibers can be not more than about 45 wt %, and optionally, can be not more than about 30 wt % to provide improved benefits. These values may impact the absorbent structure 44 by affecting the desired levels of stretchability and structural stability without excessively degrading the physical properties or the liquid-management properties of the absorbent structure. An absorbent web material with an excessively low proportion of elastomeric fibers may be insufficiently stretchable, and a web material with an excessively high proportion of elastomeric fibers may exhibit an excessive degradation of its absorbency functionalities, such as poor intake, poor distribution, poor retention of liquid.

The absorbent structure 44 may include an elastomeric coform absorbent web material. Such materials are described for instance in U.S. Pat. Nos. 6,231,557 B1 and 6,362,389 B1, which are each incorporated by reference herein to the extent they are consistent (i.e., not in conflict) herewith. In particular aspects, the elastomeric coform material can have an overall coform basis weight of at least about 50 gsm, such as up to about 1200 gsm. The coform basis weight, for example, may be at least about 100 gsm, such as at least about 200 gsm. These values can provide the absorbent structure with the desired stretchability and structural stability without excessively degrading the physical properties or the liquid-management functionalities of the absorbent structure. For example, retention portions having excessively low proportions of elastomeric coform material may not be sufficiently stretchable. Conversely, an absorbent web material having excessively large amounts of elastomeric coform materials can exhibit an excessive degradation of their absorbency functionalities, such as an excessive degradation of intake, distribution and/or retention properties.

Other examples of usable elastomeric absorbent bodies are described in international patent application WO 03/051254 and U.S. Pat. Nos. 5,964,743, 5,645,542, 6,231,557, and 6,362,389 B1, each of which are incorporated by reference herein to the extent they are consistent (i.e., not in conflict) herewith.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. An absorbent article defining a lateral direction and a longitudinal direction, the absorbent article comprising:
    an outer cover comprising an elastic material;
    a bodyside liner;
    an absorbent structure positioned in between the outer cover and the liner; and
    wherein the outer cover defining six equal distant zones in the longitudinal direction, the zones including a front waist zone, a front leg zone, a front crotch zone, a back crotch zone, a back leg zone, and a back waist zone, wherein the outer cover is constructed such that the front leg zone has a tension of less than about 1200 grams-force at about 160% to about 175% stretch in the lateral direction, and wherein each of the front waist zone, the front crotch zone, the back crotch zone, the back leg zone, and the back waist zone of the outer cover has a tension of greater than about 1500 grams-force at about 160% to about 175% stretch in the lateral direction.

2. The absorbent article as in claim 1, wherein the front leg zone has a tension of from about 300 grams-force to about 100 grams-force at about 160% to about 175% stretch in the lateral direction.

3. The absorbent article as in claim 1, wherein each of the front waist zone, the back leg zone, and the back waist zone of the outer cover has a tension of from about 1600 grams-force to about 2750 grams-force at about 160% to about 175% stretch in the lateral direction.

4. The absorbent article as in claim 1, wherein the outer cover defines apertures within the front leg zone.

5. The absorbent article as in claim 4, wherein the each of the front waist zone, the front crotch zone, the back crotch zone, the back leg zone, and the back waist zone of the outer cover are substantially free from apertures.

6. The absorbent article as in claim 4, wherein the apertures comprise linear slits directed in the longitudinal direction.

7. The absorbent article as in claim 6, wherein the linear slits have a length in the longitudinal direction of from about 1 mm to about 20 mm.

8. The absorbent article as in claim 4, wherein the apertures are substantially circular when under substantially no stretching force in any direction.

9. The absorbent article as in claim 8, wherein the apertures have a diameter of from about 0.1 mm to about 5 mm.

10. The absorbent article as in claim 4, wherein the front leg zone defines three equal distant sections in the lateral direction, the sections including two side edge sections surrounding a center section, wherein the apertures are defined in both side edge sections of the front leg zone.

11. The absorbent article as in claim 10, wherein the center section of the front leg zone is substantially free of any apertures.

12. The absorbent article as in claim 4, wherein the apertures comprise diamond shaped slits having a slit length in the longitudinal direction that is at least about twice a slit width in the lateral direction.

13. The absorbent article as in claim 1, wherein the outer cover comprises at least three pieces joined together such that the front leg zone is formed from a separate piece than the front waist zone, the front crotch zone, the back crotch zone, the back leg zone, and the back waist zone of the outer cover.

14. The absorbent article as in claim 13, wherein the front leg zone of the outer cover comprises a different material than each of the front waist zone, the front crotch zone, the back crotch zone, the back leg zone, and the back waist zone of the outer cover.

15. The absorbent article as in claim 1 further comprising an adhesive joining the outer cover, the bodyside liner, and the absorbent structure, wherein less adhesive is present in the front leg zone than in each of the front waist zone, the front crotch zone, the back crotch zone, the back leg zone, and the back waist zone.

* * * * *